(12) United States Patent
Meadowcroft et al.

(10) Patent No.: US 11,564,741 B2
(45) Date of Patent: Jan. 31, 2023

(54) ELECTROSURGICAL APPARATUS AND METHOD

(71) Applicant: CREO MEDICAL LIMITED, Chepstow (GB)

(72) Inventors: Simon Meadowcroft, Colerne (GB); Christopher Paul Hancock, Bath (GB); George Ullrich, Gwynedd (GB); David Webb, Gwynedd (GB); Louis Turner, Chepstow (GB); Julian Mark Ebbutt, Here (GB)

(73) Assignee: CREO MEDICAL LIMITED, Chepstow (GB)

( * ) Notice: Subject to any disclaimer, the term of this patent is extended or adjusted under 35 U.S.C. 154(b) by 730 days.

(21) Appl. No.: 16/089,586

(22) PCT Filed: May 30, 2017

(86) PCT No.: PCT/EP2017/062975
§ 371 (c)(1),
(2) Date: Sep. 28, 2018

(87) PCT Pub. No.: WO2017/207531
PCT Pub. Date: Dec. 7, 2017

(65) Prior Publication Data
US 2019/0110837 A1   Apr. 18, 2019

(30) Foreign Application Priority Data

May 31, 2016   (GB) ...................... 1609537

(51) Int. Cl.
*A61B 18/00* (2006.01)
*A61B 18/18* (2006.01)
*A61B 18/14* (2006.01)

(52) U.S. Cl.
CPC ...... *A61B 18/1815* (2013.01); *A61B 18/1492* (2013.01); *A61B 2018/0016* (2013.01);
(Continued)

(58) Field of Classification Search
CPC .. A61B 2018/0025; A61B 2018/00255; A61B 2018/0022; A61B 2018/00261;
(Continued)

(56) References Cited

U.S. PATENT DOCUMENTS 5,057,106 A * 10/1991 Kasevich ........... A61B 18/1815
600/549
6,080,152 A   6/2000 Nardella et al.
(Continued)

FOREIGN PATENT DOCUMENTS

GB   2487199 A   7/2012
JP   9-262245 A   10/1997
(Continued)

OTHER PUBLICATIONS

International Search Report for PCT/EP2017/062975 dated Dec. 1, 2017.
(Continued)

*Primary Examiner* — Linda C Dvorak
*Assistant Examiner* — Nicholas S Borsch
(74) *Attorney, Agent, or Firm* — ArentFox Schiff LLP

(57) ABSTRACT

An electrosurgical apparatus and method for performing thermal treatment in the gastrointestinal tract, e.g. to ablate duodenal mucosal tissue. The apparatus comprises an instrument having a flexible cable and an applicator suitable for use with a gastroscope, which can be deployed within a patient to delivery energy in a targeted or otherwise controllable manner. The applicator can deliver microwave energy by radiation. The direct and depth-limited nature of microwave energy can be make it more effective than
(Continued)

treatments that rely on thermal conduction. The applicator may include a radially extendable portion arranged to move an microwave energy delivery structure into contact with duodenal mucosal tissue at the treatment region. The applicator may comprise any of a balloon, bipolar radiator, movable paddle, and rotatable roller element.

8 Claims, 9 Drawing Sheets

(52) U.S. Cl.
CPC ............. *A61B 2018/0022* (2013.01); *A61B 2018/0025* (2013.01); *A61B 2018/00214* (2013.01); *A61B 2018/00494* (2013.01); *A61B 2018/00577* (2013.01); *A61B 2018/00785* (2013.01); *A61B 2018/183* (2013.01); *A61B 2018/1853* (2013.01); *A61B 2018/1861* (2013.01)

(58) Field of Classification Search
CPC ........... A61B 2018/00238; A61B 2018/00232; A61B 2018/1815; A61B 2018/183; A61B 2018/1853; A61B 2018/1861; A61B 2018/1876; A61B 2018/1884; A61B 2018/1823; A61B 2018/1838; A61B 2018/1846; A61B 2018/00315; A61B 2018/00482; A61B 2018/00494; A61B 1/273; A61B 1/2733; A61B 1/2736
See application file for complete search history.

(56) References Cited

U.S. PATENT DOCUMENTS

| | | | |
|---|---|---|---|
| 6,176,857 B1 | 1/2001 | Ashley | |
| 6,494,881 B1 | 12/2002 | Bales et al. | |
| 9,855,098 B2* | 1/2018 | Rioux | A61B 18/1492 |
| 2002/0019627 A1 | 2/2002 | Maguire et al. | |
| 2002/0032441 A1 | 3/2002 | Ingle et al. | |
| 2002/0065530 A1* | 5/2002 | Mische | A61M 25/10 |
| | | | 606/151 |
| 2002/0072742 A1 | 6/2002 | Schaefer et al. | |
| 2002/0091427 A1* | 7/2002 | Rappaport | A61B 18/18 |
| | | | 604/20 |
| 2003/0130653 A1 | 7/2003 | Sixto, Jr. et al. | |
| 2003/0195604 A1* | 10/2003 | Ingle | A61N 1/06 |
| | | | 607/138 |
| 2004/0186468 A1 | 9/2004 | Edwards | |
| 2005/0149012 A1 | 7/2005 | Penny et al. | |
| 2005/0171525 A1* | 8/2005 | Rioux | A61B 18/1492 |
| | | | 606/41 |
| 2008/0275445 A1* | 11/2008 | Kelly | A61B 18/18 |
| | | | 606/45 |
| 2009/0012513 A1 | 1/2009 | Utley et al. | |
| 2010/0004650 A1 | 1/2010 | Ormsby et al. | |
| 2010/0168727 A1 | 7/2010 | Hancock et al. | |
| 2012/0029326 A1 | 2/2012 | Kawamura et al. | |
| 2012/0116486 A1 | 5/2012 | Naga et al. | |
| 2012/0197154 A1 | 8/2012 | Reeves et al. | |
| 2012/0197245 A1 | 8/2012 | Burnett et al. | |
| 2012/0259326 A1* | 10/2012 | Brannan | A61B 17/00234 |
| | | | 606/33 |
| 2013/0178844 A1 | 7/2013 | Lee et al. | |
| 2013/0197555 A1 | 8/2013 | Schaer | |
| 2013/0211176 A1 | 8/2013 | Habib | |
| 2013/0267943 A1 | 10/2013 | Hancock | |
| 2013/0289557 A1* | 10/2013 | Hancock | H01Q 13/08 |
| | | | 606/33 |
| 2014/0364848 A1 | 12/2014 | Heimbecher et al. | |
| 2014/0371736 A1 | 12/2014 | Levin et al. | |
| 2015/0141987 A1 | 5/2015 | Caplan et al. | |
| 2015/0305809 A1 | 10/2015 | Prakash et al. | |
| 2015/0374436 A1* | 12/2015 | Subramaniam | A61B 18/1492 |
| | | | 606/41 |
| 2016/0113700 A1 | 4/2016 | Hancock et al. | |

FOREIGN PATENT DOCUMENTS

| | | | |
|---|---|---|---|
| JP | 2006-181353 A | | 7/2006 |
| JP | 2008-541878 A | | 11/2008 |
| JP | 2009-527331 A | | 7/2009 |
| KR | 10-2015-0014459 A | | 2/2015 |
| WO | WO 2013/160772 A2 | | 10/2013 |
| WO | WO 2014/102857 A1 | | 7/2014 |
| WO | WO 2015/038973 A1 | | 3/2015 |

OTHER PUBLICATIONS

Search Report in United Kingdom Application No. GB 1609537.4 dated Feb. 9, 2017.

Search Report in United Kingdon Application No. GB 1609537.4 dated Nov. 25, 2016.

* cited by examiner

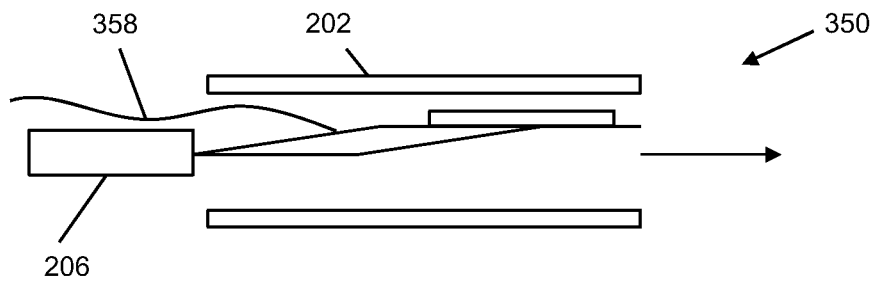
Fig. 9A
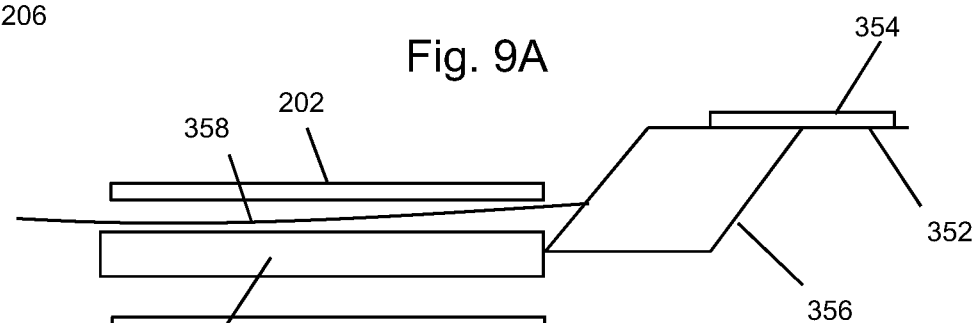
Fig. 9B
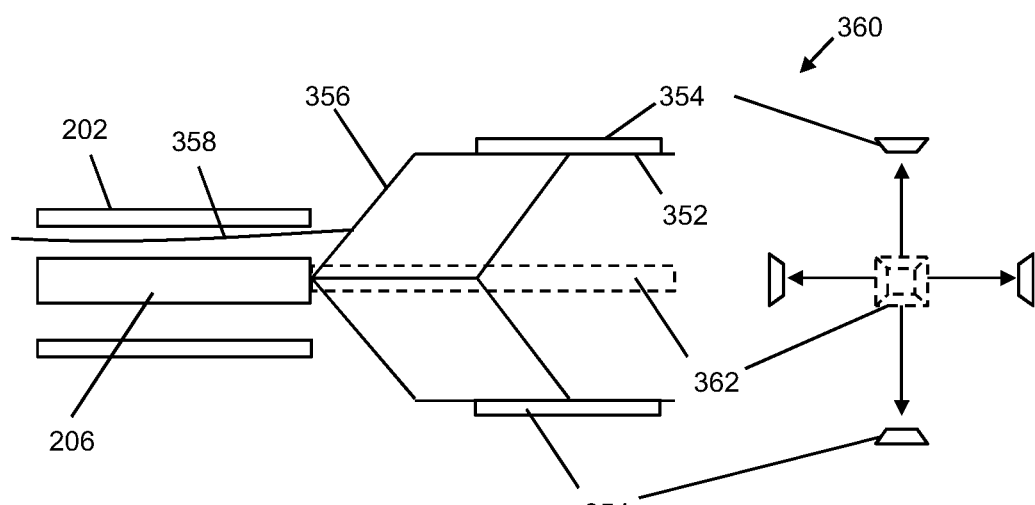
Fig. 10A
Fig. 10B

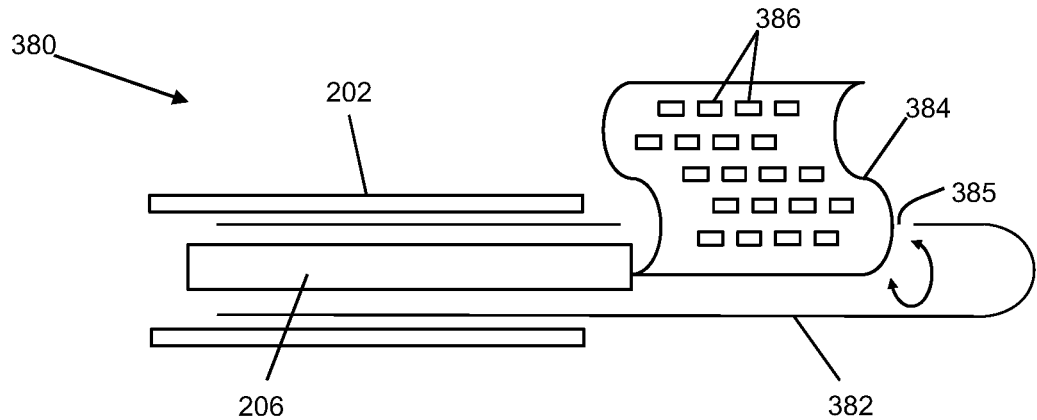
Fig. 11
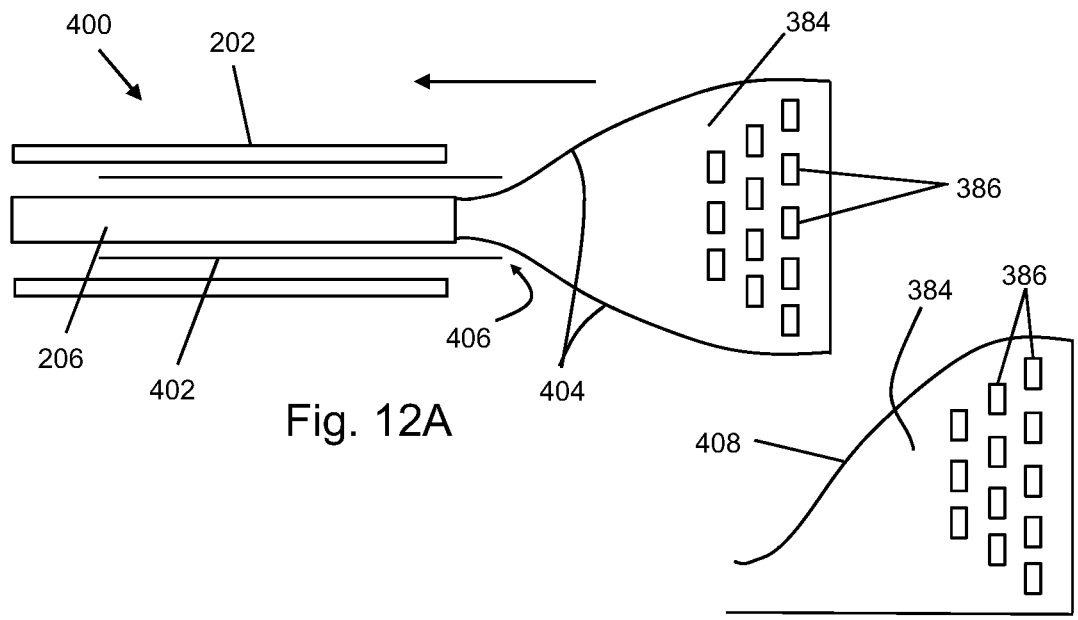
Fig. 12A
Fig. 12B
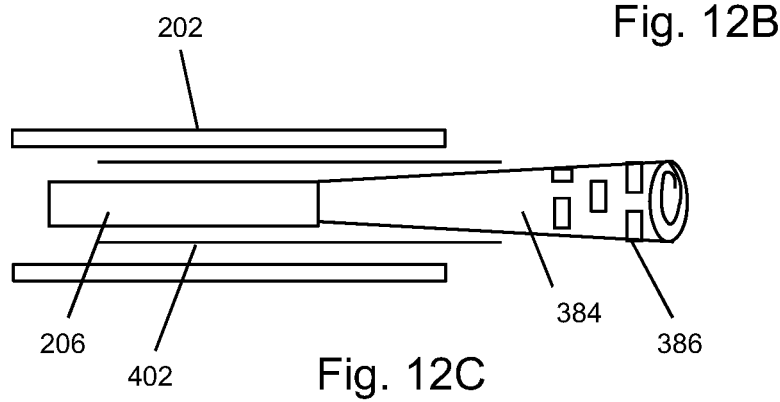
Fig. 12C

ELECTROSURGICAL APPARATUS AND METHOD

CROSS-REFERENCE TO RELATED APPLICATIONS

This application is a National Stage entry of International Application No. PCT/EP2017/062975, filed on May 30, 2017, which claims priority to United Kingdom Patent Application No. 1609537.4, filed on May 31, 2016. The disclosures of the priority applications are incorporated in their entirety herein by reference.

FIELD OF THE INVENTION

The invention relates to an electrosurgical apparatus and method for treating biological tissue with microwave energy. In particular, the present invention is concerned with delivering microwave energy to biological tissue in the gastrointestinal tract, especially the duodenum. In one example, the invention provides an electrosurgical instrument adapted to controllably deliver microwave energy to ablate or resurface a wall of the duodenum.

BACKGROUND TO THE INVENTION

There is a lot of interest in the potential treatment of Type 2 (T2) diabetes. This is a rapidly increasing problem in most developed countries because of obesity and a more sedentary lifestyle. It is also contributing to significant healthcare spend. Nearly 20% of the NHS budget is spent on diabetes and its co-morbidities.

At present, diabetes is typically only identified and managed. Other than major reconstructive gastrointestinal surgery, there is no treatment.

However, more recent research in this field has investigated resurfacing the duodenum by applying thermal energy to the wall of the duodenum. The thermal energy is applied by delivering hot water to a balloon inserted to an appropriate location in the gastrointestinal tract. The thermal energy acts to ablate the duodenum's mucosa. Early results indicate triggering regrowth of the mucosa in this way can change the way the body responds to sugar in a manner that can restore metabolic health, and, in particular, reverse a resistance to insulin [1]. This technology represents a possible treatment for T2 diabetes.

SUMMARY OF THE INVENTION

At its most general, the present invention presents an electrosurgical apparatus and method for effective and efficient thermal treatment in the gastrointestinal (GI) tract. In particular, the invention provide an electrosurgical apparatus having an applicator suitable for use with a gastroscope or the like, which can be deployed within a patient to delivery energy in a targeted or otherwise controllable manner.

In some examples, the applicator is arranged to deliver microwave energy, e.g. by radiation, which is directly received by biological tissue. An advantage of using microwave energy is that the depth which it penetrates into tissue is shallow, which can ensure that only the surface of the GI tract is affected. The direct and depth-limited nature of microwave energy can be make it more effective than treatments that rely on thermal conduction.

According to one aspect, the present invention may provide an electrosurgical instrument configured to ablate duodenal mucosal tissue, the instrument comprising: a flexible coaxial cable for conveying microwave energy from a generator located externally to the patient to a treatment site located inside a patient's duodenum; and an applicator located at a distal end of the flexible coaxial cable, the applicator having an energy delivery structure connected to receive microwave energy from the coaxial cable and to deliver the received microwave energy into biological tissue at the treatment site, wherein the applicator includes a radially extendable portion arranged to move the energy delivery structure into contact with duodenal mucosal tissue at the treatment region. A method of treating duodenal mucosal tissue with microwave energy, e.g. using such an instrument, may be an independent aspect of the invention. The application of microwave energy may also be used to treat tissue below the surface, e.g. to perform tissue modification or denaturing in one or more submucosal layers.

The applicator may comprise a balloon, e.g. formed form a resiliently deformable (e.g. stretchy) dielectric material. The balloon may be inflatable, e.g. by filling it with an inflation medium, which may be a gas or liquid. An inflation channel may run in or alongside the coaxial cable to deliver the inflation medium. The properties (e.g. relative permittivity or the like) of the inflation medium may be selected to facilitate delivery of the microwave energy.

The balloon may be or may carry the energy delivery structure. For example, the energy delivery structure may comprise a portion of an inner conductor of the flexible coaxial cable that protrudes into the volume enclosed by the balloon to form a monopole antenna for launching the microwave energy into biological tissue at the treatment site. The field emitted by the monopolar antenna may be shaped by providing conductive material on the surface of the balloon.

Alternatively, the balloon may form part of or may carry a bipolar-type microwave energy delivery structure. For example, an outer conductive structure may be formed on an outer surface of the balloon. The outer conductive structure may be grounded, e.g. by being electrically connected to an outer conductor of the flexible coaxial cable.

The energy delivery structure may comprise a bipolar microwave emitting structure formed by the outer conductive structure and an internal conductive element located inside the volume enclosed by the balloon, the internal conductive element being electrically connected to an inner conductor of the coaxial cable. The inner conductive element may be an extension of the inner conductor of the coaxial cable, or it may be a conductive loop arranged to match the shape of the balloon when in an inflated configuration. Alternatively, the inner conductive element may be a conductive layer formed on an internal surface of the balloon, whereby the balloon skin is a dielectric material in a bipolar radiating structure. In another example, the inner conductive element may be a conductive layer formed on an outer surface of an auxiliary inflatable balloon located within the volume enclosed by the balloon. A dielectric material, e.g. low density PFTE or other low loss material, may be enclosed in the volume between the outer surface of the auxiliary balloon and the inner surface of the (main) balloon.

The bipolar microwave emitting structure may operate as a slotted radiator, e.g. by providing a plurality of radiating slots in the outer conductive structure.

The conductive structures may be metallisation layers, e.g. of Ag, Au, Pt, Cu or Ag-plated Cu, formed on the balloon skin.

In some examples, the material of the balloon forms part of the bipolar microwave emitting structure, but this need not be essential. For example, the balloon may act as a transport mechanism for moving energy delivery structures that are mounted thereon into close proximity or contact with the tissue to be treated. In one example, the radiating structures fabricated using flexible dielectric material (discussed in more detail below) may be mounted on an outer surface of the balloon.

In another example, the applicator may comprise a paddle and a movement mechanism configured to move the paddle in a radial direction, and wherein the energy delivery structure comprises a bipolar antenna mounted on the paddle. The paddle may be a flat or flexible elongate structure arranged to lie along, e.g. in contact with, the wall of the GI tract (and in particular, the duodenum). The structure may resemble one half of an forceps, which the bipolar antenna arrange to radiate radially outwardly. The bipolar antenna may have a structure similar to that used in the electrosurgical forceps described in WO 2015/097472 or WO 2015/052502.

There may be a plurality of paddles arranged to move in radial directions that are angularly offset from each other. For example, there may be four paddles which move in directions that are 90° from each other. One or more of the plurality of paddles may be inactive, i.e. not have an energy delivery structure formed thereon or associated therewith. Alternatively, each of the plurality of paddles may be independently activatable, so that directional treatment is possible. The convoluted nature of a tissue surface in the duodenum may make it desirable for the applicator to apply a lateral force to distend and flatten the treatment surface area. Inactive paddles can be used for this purpose. This may be particularly useful for treatment in and around areas such as the major/minor papilla of the bile ducts.

The movement mechanism may be controlled by a control rod or pull wire that extends along the coaxial cable. The movement mechanism may comprise a hinge mechanism, e.g. in the form of a pantograph or the like, that transforms a longitudinal pull force into radial outward movement of the paddle(s).

The energy delivery structure may comprise a flexible dielectric substrate having: a conductive layer formed on a first surface thereof, the conductive layer being electrically connected to an inner conductor of the coaxial cable, and a plurality of conductive elements formed on a second surface thereof, wherein the plurality of conductive elements are electrically grounded and dimensioned to act as radiating elements for the microwave energy received by the energy delivery structure. The plurality of conductive elements may be configured, e.g. dimensioned, as leaky feeders or as radiating patch antennas.

The flexible dielectric substrate may be in the form of a sheet, and the plurality of conductive elements are arranged in a two-dimensional array on the sheet. The sheet may be rollable into a cylindrical form.

Alternatively, the flexible dielectric substrate may be in the form of one or more strips, where the plurality of conductive elements are arranged in a row along each strip. The applicator may be arranged to deploy one or more of these strips in different ways. For example, a strip may take the form of a retractable loop, or a helical coil. In another example, a plurality of longitudinally arranged flexible strips may be arranged to flex radially outward upon application of a deployment force.

In another aspect, the invention may provide an electrosurgical apparatus for ablating duodenal mucosal tissue, the apparatus comprising: a surgical scoping device (e.g. a gastroscope) having an instrument cord for insertion in a patient to a treatment site located inside the patient's duodenum; a generator for supplying microwave energy; and an electrosurgical instrument as described above, wherein the flexible coaxial cable is connected at its proximal end to the generator, and wherein the flexible coaxial cable and applicator are insertable together with the instrument cord to the treatment site. The instrument cord has a longitudinal instrument channel running therethrough. In a preferred arrangement, the flexible coaxial cable and applicator may be dimensioned to be slidably mounted in the instrument channel. However, in other examples, the applicator may not travel through the instrument channel before treatment. A carrier may be provided at or adjacent a distal end of the instrument cord for holding the applicator. Similarly, the flexible coaxial cable and any other feed required by the applicator may or may not travel through the instrument channel.

In another aspect, the present invention may provide an electrosurgical instrument for delivering energy to resurface biological tissue in a patient's gastrointestinal tract, the instrument comprising: a flexible coaxial cable for conveying microwave energy from a generator located externally to the patient to a treatment site located inside the patient's gastrointestinal tract; and an applicator located at a distal end of the flexible coaxial cable, the applicator having an energy delivery structure connected to receive microwave energy from the coaxial cable and to deliver the received microwave energy into biological tissue at the treatment site, wherein the applicator comprises a rotatable radiating structure that is rollable along biological tissue at the treatment site.

The applicator may comprise a probe housing that encloses the coaxial cable, wherein the radiating structure is rotatably mounted at a distal end of the probe housing. The radiating structure may be in the shape of a cylinder or ball having a laterally oriented rotation axis.

The radiating structure comprises: an inner conductive ring electrically connected to an inner conductor of the coaxial cable, a dielectric annular element mounted to cover the inner conducive ring around the circumference of the radiating structure, and a plurality of grounded conductive patches formed on an outer surface of the annular element. The conductive patches may act as radiating antennas or as a leaky feeder.

In another aspect, the invention may provide an electrosurgical instrument for delivering energy to resurface biological tissue in a patient's gastrointestinal tract, the instrument comprising: a flexible coaxial cable for conveying microwave energy from a generator located externally to the patient to a treatment site located inside the patient's gastrointestinal tract; and an applicator located at a distal end of the flexible coaxial cable, the applicator having an energy delivery structure connected to receive microwave energy from the coaxial cable; and a gas feed arranged to convey gas to the applicator from a gas supply located externally to the patient, wherein the applicator is arranged to deliver the received microwave energy into the gas received at the applicator to strike or sustain a plasma for delivery to biological tissue at the treatment site.

The applicator may comprise a probe housing that encloses the coaxial cable and defines a gas flow path in communication with the gas feed, the probe housing having one or more gas exit apertures at its distal end. An electric field may be set up within the probe housing to strike a plasma at the gas exit apertures. For example, the probe housing may be electrically connected to an outer conductor of the coaxial cable, and the energy delivery structure may comprise a conductive element extending within the probe housing away from a distal end of the coaxial cable and electrically connected to an inner conductor of the coaxial cable. The conductive element may be electrically connected to a distal tip of the probe housing to set up a short circuit condition in which an electric field exhibits maxima at predetermined distances from the point of contact at the distal tip. The gas exit apertures may be located at the electric field maxima to enable the plasma to be struck.

Other aspects of the invention may use different energy sources. For example, in one aspect the invention may provided a surgical instrument for delivering energy to a surface of a patient's gastrointestinal tract, the instrument comprising: a flexible energy feed cable for conveying energy from an energy source locating externally to the patient to a treatment site; and an applicator located at a distal end of the flexible energy feed cable, wherein the flexible energy feed cable comprises a bundle of graphene cables, and wherein the applicator comprises an array of graphene cable terminations for delivering thermal energy into biological tissue at the treatment site.

In another aspect, the invention may provide a surgical instrument for delivering energy to a surface of a patient's gastrointestinal tract, the instrument comprising: a flexible energy feed cable for conveying energy from an energy source locating externally to the patient to a treatment site; and an applicator located at a distal end of the flexible energy feed cable, wherein the applicator comprises a thermoelectric device arranged to introduce a thermal gradient at the treatment site thereby to deliver thermal energy into biological tissue at the treatment site.

The disclosure herein also discusses a carrier structure securing a surgical device (e.g. an applicator as discussed herein) to a distal end of an instrument cord of a surgical scoping device. The carrier structure may comprise a flexible or deformable support, e.g. a cup-shaped or recessed housing, that is secured at the distal end of the instrument cord and either projects distally away therefrom or lies therearound. The carrier structure may be clipped onto the instrument cord, e.g. using an annular ring. In other examples, the carrier structure may be adhered to the instrument cord or formed integrally with it.

The carrier structure may extend along the length of the instrument cord. For example, it may be a sleeve that extends alongside the whole length of the instrument cord and is secured (e.g. clipped) thereto at intervals along its length. Alternatively, the carrier structure may be a sleeve that encloses (i.e. defines a lumen for carrying) the instrument cord.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. A frequency of 14.5 GHz may be preferred due to its depth of penetration into biological tissue in the gastrointestinal tract, and in particular in the wall of the duodenum.

References herein to "conductive" material or "conductors" relate to electrical conductivity unless the context makes clear otherwise.

BRIEF DESCRIPTION OF THE DRAWINGS

Embodiments of the invention are discussed below with reference to the accompanying drawings, in which:

FIGS. 9A and 9B are schematic side views of a distal end assembly having a radially extendable paddle structure that is another embodiment of the invention;

FIGS. 10A and 10B are a schematic illustration of a distal end assembly for an electrosurgical instrument having a plurality of radially extendable paddles.

FIG. 11 is a schematic side view of a distal end assembly for an electrosurgical instrument which comprises a rollable flexible substrate that is another embodiment of the invention;

FIGS. 12A, 12B and 12C illustrate schematic side views of a distal end assembly having a flexible substrate suitable for use in an electrosurgical instrument that is another embodiment of the invention;

DETAILED DESCRIPTION; FURTHER OPTIONS AND PREFERENCES

Figure 1:
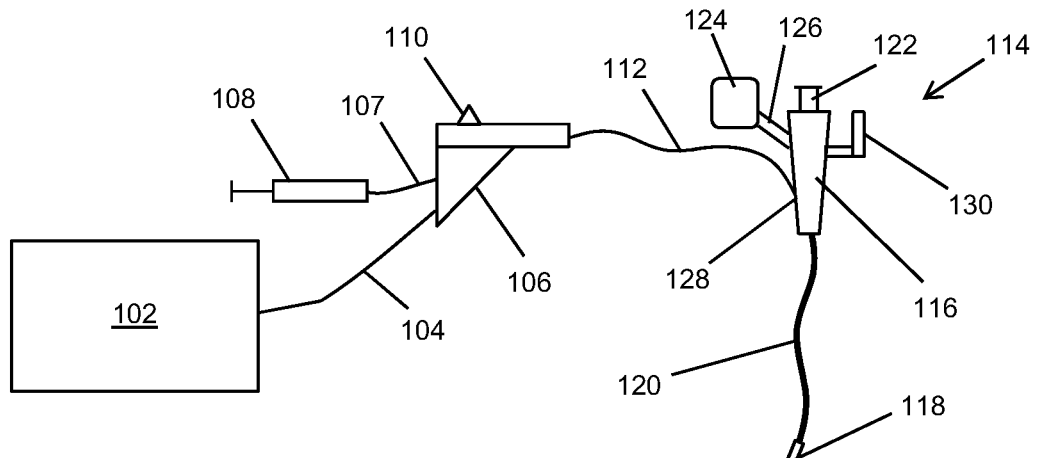
FIG. 1 is a schematic diagram showing an electrosurgery system for use in an embodiment of the invention.

FIG. 1 is a schematic diagram of a complete electrosurgery system 100 that is capable of supplying electromagnetic energy (e.g. microwave energy) to the distal end of an electrosurgical instrument. The system 100 comprises a generator 102 for controllably supplying energy, which may be any one or more of microwave energy, thermal energy (e.g. infrared radiation), or electrical energy (e.g. a DC current). In one example, the generator 102 may take the form of that described in WO 2012/076844, which is arranged to deliver microwave energy. The generator 102 may be arranged to monitor reflected signals (i.e. reflected power) received back from the electrosurgical instrument in order to determine an appropriate signal to be conveyed to the instrument.

The generator 102 is connected to an interface joint 106 by an interface cable 104. The interface joint 106 may also be connected to receive a fluid supply 107 from a fluid delivery device 108, such as a syringe, e.g. for inflating an expandable applicator using liquid or gas (e.g. air), as discussed below. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of an instrument (working) channel of a surgical scoping device 114, such as an endoscope, gastroscope, laparoscope or the like. For treatment of the duodenum contemplated herein, a gastroscope may be preferred.

The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is the instrument channel discussed above. Other lumens may include a channel for conveying optical radiation, e.g. to provide illumination at the distal end and or to gather images from the distal end. The body 116 may include a eye piece 122 for viewing the distal end. In order to provide illumination at the distal end, a light source 124 (e.g. LED or the like) may be connected to the body 116 by an illumination input port 126.

The flexible shaft 112 has a distal assembly 118 (not drawn to scale in FIG. 1) that is shaped to pass through the instrument channel of the surgical scoping device 114 and protrude (e.g. inside the patient) at the distal end thereof. The distal end assembly includes means for delivering energy from the generator 102 into biological tissue.

The structure of the distal assembly 118 may be arranged to have a maximum outer diameter suitable for passing through the instrument channel. Typically, the diameter of an instrument channel in a gastroscope is less than 4.0 mm, e.g. any one of 2.8 mm, 3.2 mm, 3.7 mm, 3.8 mm. The length of the flexible shaft can be equal to or greater than 1.2 m, e.g. 2 m or more. In other examples, the distal assembly 118 may be mounted at the distal end of the flexible shaft 112 after the shaft has been inserted through the instrument channel (and before the instrument cord is introduced into the patient). Alternatively, the flexible shaft 112 can be inserted into the instrument channel from the distal end before making its proximal connections. In these arrangement, the distal end assembly 118 can be permitted to have dimensions greater than the instrument channel of the surgical scoping device 114.

If the energy from the generator 102 is microwave energy, the body 116 includes a power input port 128 for connecting to the flexible shaft, which comprises a coaxial cable (e.g. a conventional coaxial cable) capable of conveying the radiofrequency and microwave energy from the generator 102 to the distal assembly 118.

It may be desirable to control the position of at least the distal end of the instrument cord 120. The body 116 may include a control actuator 130 that is mechanically coupled to the distal end of the instrument cord 120 by one or more control wires (not shown), which extend through the instrument cord 120. The control wires may travel within the instrument channel or within their own dedicated channels. The control actuator 130 may be a lever or rotatable knob, or any other known catheter manipulation device. The manipulation of the instrument cord 120 may be software-assisted, e.g. using a virtual three-dimensional map assembled from computer tomography (CT) images.

In the following discussion, a number of different configurations are described for the distal assembly 118 mentioned above. Herein, the distal assembly 118 may be referred to as a distal end assembly or an applicator. Its function is to deliver energy, e.g. microwave energy, thermal energy or the like, into biological tissue.

The examples discussed below can be separated into applicators that are arranged to deliver microwave energy, and that applicators that are arranged to deliver thermal energy (e.g. infrared radiation) or to excite other thermal effects in the biological tissue. We begin with a discussion of the applicator structures which utilise microwave energy, which are described in FIGS. 2 to 14.

FIGS. 2 to 7 illustrate a number of applicator structures which utilise an expandable balloon at the distal end of the instrument channel. As shown in FIG. 2A, an applicator structure 200 of this type may comprise a sleeve 202 that sits within the instrument channel of the scoping device, which defines a lumen 204 through which various components of the applicator are carried. FIG. 2A (and subsequent drawings) shows only a short distal section of the sleeve 202. It can be understood that sleeve 202 may extend for the entire length of the instrument channel. In the example shown in FIG. 2A, lumen 204 carries a coaxial cable 206 and an inflation tube 208. The inflation tube may be integrated into the coaxial cable 206, e.g. as a hollow passage through the centre of an inner conductor of the coaxial cable 206. A proximal end of the inflation channel 208 is connected to a fluid (liquid or gas) supply.

A flexible balloon structure is mounted on the distal end of the coaxial cable 206. The flexible balloon structure comprises a deformable (e.g. elastic) skin 210 that defines an enclosed volume at a distal end of the coaxial cable 206. The inner conductor 212 of a coaxial cable extends into the volume defined by the skin 210. The inflation channel 208 has an aperture at its distal end that provides fluid communication to the enclosed volume. Fluid may be delivered through the inflation channel 208 to expand (inflate) or retract (deflate) the balloon. The applicator 200 may be arranged so that the coaxial cable 208 and balloon are moveable relative to the sleeve 202. For example, the sleeve 202 may be retractable relative to the coaxial cable to expose the balloon.

Figure 2A:
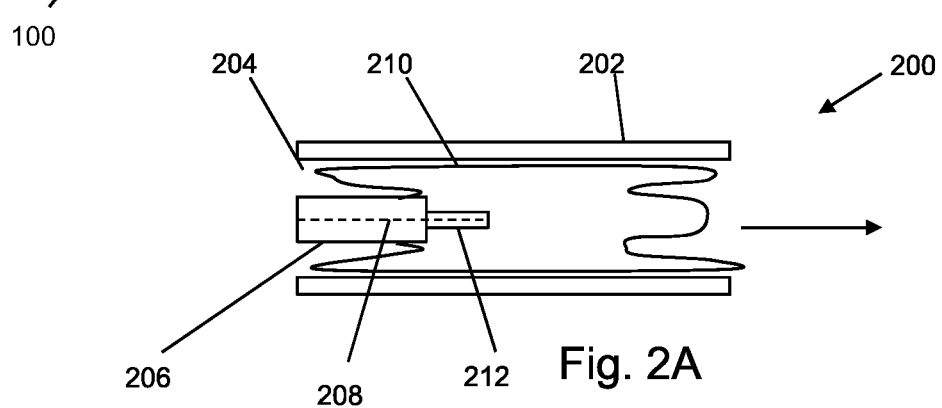
FIGS. 2A and 2B are schematic cross-sectional views of a distal end assembly for an electrosurgical system as shown in FIG. 1 in a retracted and expanded configuration respectively.
Figure 2B:
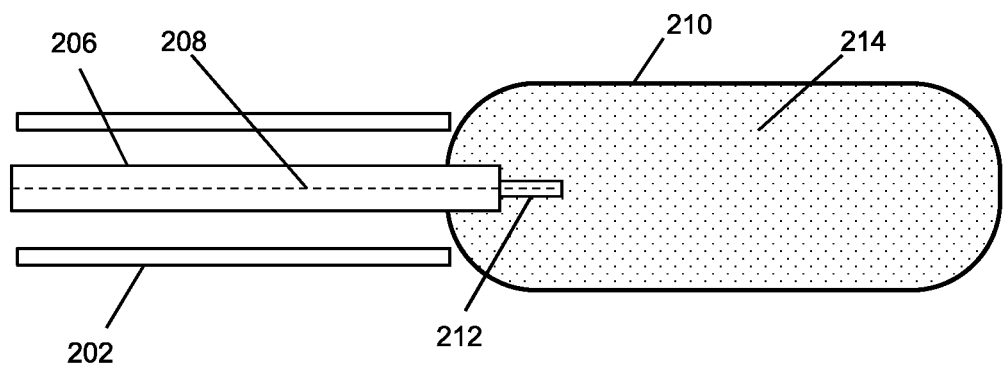

FIG. 2B shows the applicator 200 in an expanded configuration, where the sleeve 202 has moved proximally relative to the coaxial cable 206 in order to expose the balloon. An inflation medium has been supplied through the inflation channel 208 to expand the balloon. In this example, the coaxial cable 206 is arranged to convey microwave energy. The exposed portion of the inner conductor 212 at the distal end of the coaxial cable acts as a monopole antenna. The inflation medium 214 may be a low loss material arranged to facilitate efficient transfer of microwave energy to the skin 210 of the balloon.

In use, the applicator 200 may be positioned within the GI tract (e.g. in the duodenum) when in the retracted position shown in FIG. 2A. Once in position, the applicator 200 may be changed into the expanded configuration shown in FIG. 2B. Upon moving to the expanded configuration, the balloon may extend radially outwards to come into contact with the wall of the GI tract. The skin 210 may stretch so that a good contact is formed between the balloon and the biological tissue. In this manner, the applicator 200 may be capable of delivering a uniform dose of microwave energy around the circumference of the balloon to ablate or resurface biological tissue surrounding it.

The low loss material 214 may be air, or low density PTFE, or a foam. Providing a low loss material ensures that the loss of microwave energy into the inflation medium 214 does not cause unwanted heating of the inflation medium.

The inflatable balloon may take any shape. The shape selected may depend on the type of treatment desired. For example, the balloon may have an elongate cylindrical shape if circumferential treatment along a section of the GI tract is desired. In other embodiments, the balloon may be shorter (e.g. spherical) to restrict the longitudinal extent of treatment.

Figure 3:
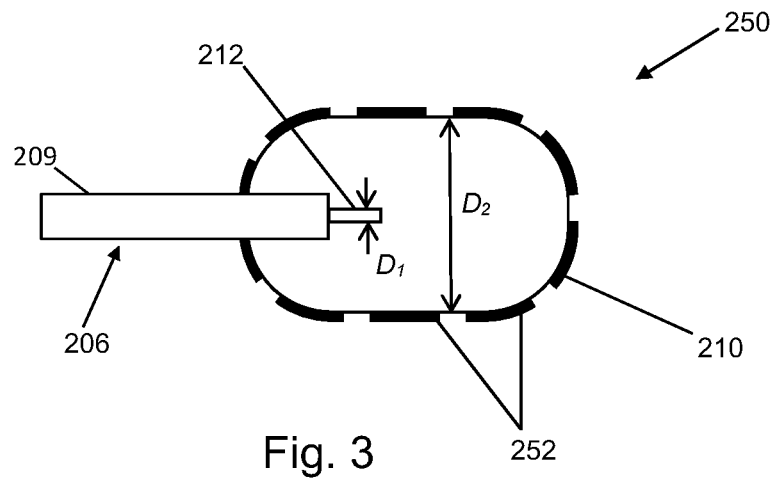
FIG. 3 shows an expandable balloon applicator structure suitable for use in an electrosurgical instrument that is an embodiment of the invention.

FIG. 3 is a schematic and partial cross-sectional view of another applicator 250 that incorporates an inflatable balloon. Features in common with the device shown in FIGS. 2A and 2B are given the same reference numbers and are not described again. The sleeve and inflation channel are omitted for clarity. The applicator 250 is configured as a "slotted" radiator. A plurality of conductive elements 252 are fabricated on the skin 210 of the balloon. For example, the conductive elements 252 may be metallised regions or patches on the outside of the balloon. The conductive elements 252 may be electrically connected to the outer conductor 209 of the coaxial cable 206. The conductive elements 252 serve to restrict the delivery of microwave energy. In the embodiment shown in FIG. 3, the microwave energy is delivered from the gaps (slots) between the conductive elements 252. In this way, a desired pattern of treatment can be obtained by suitably configuring the shape and location of the conductive elements 252. For example, one side of the balloon may be metallised to shield on side of the GI tract from the microwave energy. The metallised portions may be capable of expanding with the balloon as it inflates. For example the conductive elements 252 may be formed from a metallised flexible polymer layer.

In any of the balloon-based applicator structures disclosed herein, the shape and configuration of the inflatable balloon may be arranged to act as an impedance transformer to aid efficient coupling of the microwave energy from the coaxial cable 206 into the biological tissue.

In a matched condition, the impedances satisfy the following relation:

$$Z_t = \frac{Z_0^2}{Z_a} \quad (1)$$

wherein $Z_t$ is the tissue impedance, $Z_0$ is the characteristic impedance of the coaxial cable, and $Z_a$ is the impedance of the applicator. For the applicator structure shown in FIG. 3, $Z_a$ can be expressed as $$Z_a = \frac{138}{\sqrt{\varepsilon_r}} \log_{10} \frac{D_2}{D_1} \quad (2)$$

wherein $\varepsilon_r$ is the relative permittivity of the material in the balloon, $D_1$ is the outer diameter of the inner conductor, and $D_2$ is the diametric spacing of the inner surfaces of the conductive elements mounted on the surface of the balloon. Accordingly, by suitable selection of the balloon geometry and the material that inflates the balloon, the applicator structure 250 can be arranged to efficiently deliver microwave energy into biological tissue.

Figure 4:
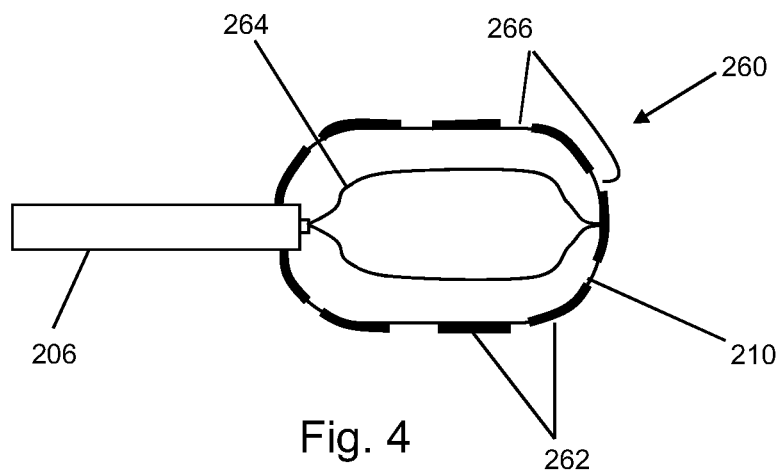
FIG. 4 shows an expandable balloon applicator structure suitable for use in an electrosurgical instrument that is another embodiment of the invention.

FIG. 4 is a schematic and partial cross-sectional view of another applicator 260 that can be used in the invention. Again, features in common with the applicators discussed above are given the same reference numbers and are not described again. The sleeve and inflation channel are also omitted in FIG. 4 for clarity.

The applicator 260 in FIG. 4 has a structure similar to that shown in FIG. 3, in that a conductive structure 262 is provided on the surface of the balloon skin 210. However, in this embodiment, the inner conductor 212 of the coaxial cable 206 does not launch energy into a volume defined by the balloon skin 210. Instead, an electrically conductive connector, which in this example is a wire loop 264, extends beyond a distal end of the coaxial cable 206 to connect the inner conductor to a distal end of the conductive structure 262, which in turn has a proximal end connected to the outer conductor (e.g. outer conductor 209) of the coaxial cable 206. This creates a short circuit condition. Slots 266 are provided in the conductive structure 262 at locations which correspond to maxima of the electric field that is generated as a result of the short circuit condition. Thus, the first slot is spaced by a quarter of a wavelength from a connection point between the wire loop 264 and outer conductive structure 262. Subsequent slots 266 are spaced apart by half a wavelength. In this case, the wavelength depends on the dielectric properties of the inflation medium. Accordingly, by suitable selection of the inflation medium and the slots basing, the structure shown in FIG. 4 can efficiently radiate microwave energy.

Figure 5:
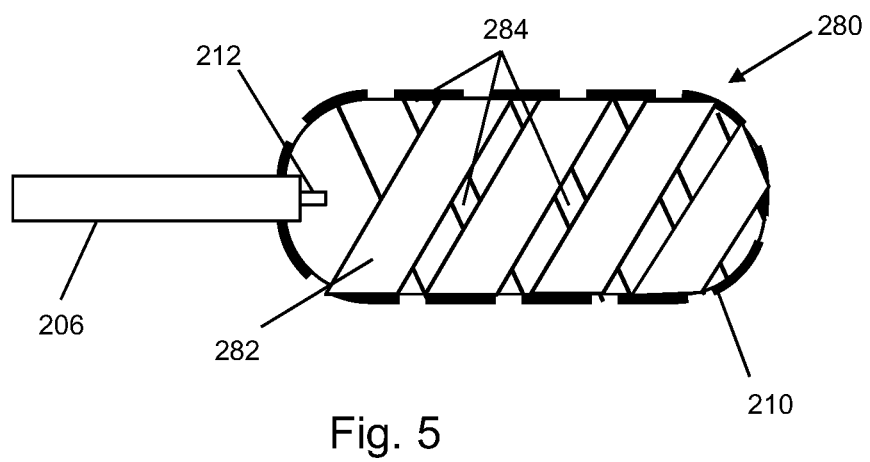
FIG. 5 shows a schematic view of another expandable balloon applicator structure suitable for use in an electrosurgical instrument that is an embodiment of the invention.

FIG. 5 shows a schematic side view of an applicator 280 that can be used in another embodiment of the invention. As before, features in common with previous examples are given the same references number, and are not described again. The applicator 280 is similar to the example shown in FIG. 3. The inner conductor 212 of the coaxial cable 206 protrudes inside the inflatable balloon which is formed of expandable skin 210. The inflation channel for inflating the balloon is omitted for clarity.

In this example, an electrically conductive structure 282 having a collapsible configuration is formed or mounted on the outer surface of the expandable skin 210. The electrically conductive structure 282 comprises a two sets of conductive bands that are wound around the circumference of the balloon. Each set comprises a plurality of parallel bands that are spaced apart in a longitudinal direction. The bands in a first set lie over the bands in a second set in a criss-cross manner. The width of the bands is selected so that on inflating the balloon, gaps 284 appear adjacent the junction at which the bands intersect. In the example, the gaps 284 have a diamond shape. The expandable skin 210 is exposed in the gaps, which present radiating holes through which the microwave energy can be delivered. The criss-cross nature of the bands provides sufficient flexibility for the balloon when in a deflated (retracted) configuration in order to assist withdrawal through the instrument channel or back into the sleeve (not shown).

In the example shown in FIG. 5, the bands of conductive material 282 may be connected to the outer conductor (e.g. outer conductor 209) of the co-axial feed cable 206. In order for the structure shown in FIG. 5 to operate as a leaky feeder-type energy delivery structure, the width of the electrically conductive bands may be set to be half a wavelength of the microwave energy whereas the gaps 284 may have a largest dimension equal to or less than ⅛ th of the wavelength of the wavelength. As discussed above, the wavelength of the microwave energy depends on the inflating medium contained within the inflatable skin 210. Accordingly, by selecting the inflating medium in conjunction with the sizes of the electrically conductive bands and gaps that appear on the surface of the balloon when inflated, the structure as shown in FIG. 5 can be made to operate as a leaky feeder.

Figure 6:
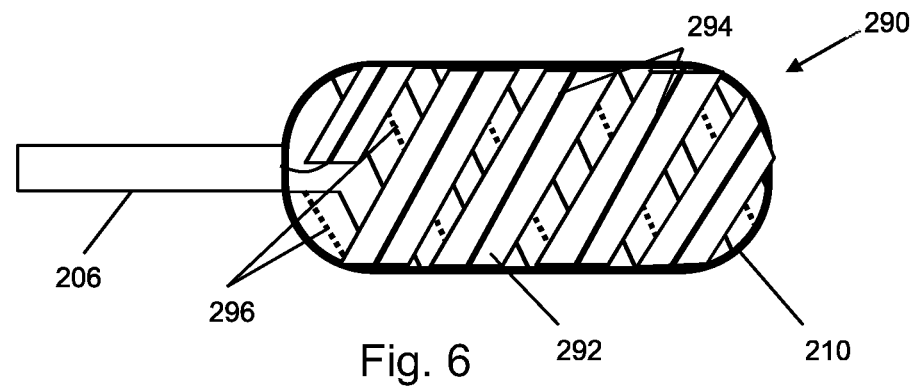
FIG. 6 shows another expandable balloon applicator suitable for use in an electrosurgical instrument that is an embodiment of the invention.

FIG. 6 shows a schematic side view of another applicator 290 that can be used in an electrosurgical instrument according to an embodiment of the invention. As before, features in common with earlier embodiments are given the same reference number, and are not described again. The sleeve and inflation channel are omitted for clarity.

The applicator 290 shown in FIG. 6 is similar to the applicator 280 of FIG. 5 in that includes a series of criss-crossed circumferential bands formed on the outer surface of the inflatable skin 210. However, in this embodiment the inner conductor 212 of the coaxial cable 206 is not arranged to launch the microwave energy into the internal volume of the balloon. Instead, the criss-crossed bands are formed from strips of dielectric (insulating) material 292 having a thin conductive strip formed thereon. The criss-crossed strips comprise a top strip wound in one direction around the circumference of the balloon, and a bottom strip round in an opposite direction. The conductive strips on each of these bands is connected to a different conductor of the coaxial cable 206. Thus, in the example shown, the conductive strip 294 on the top band is connected to the inner conductor, and the conductive strip 296 on the bottom band is connected to the outer conductor (e.g. outer conductor 209). In this arrangement, radiating microstrip type structures are formed at the junctions where the top most layer passes over the bottom most layer. These junctions can therefore radiate microwave energy into surrounding tissue.

Figure 7:
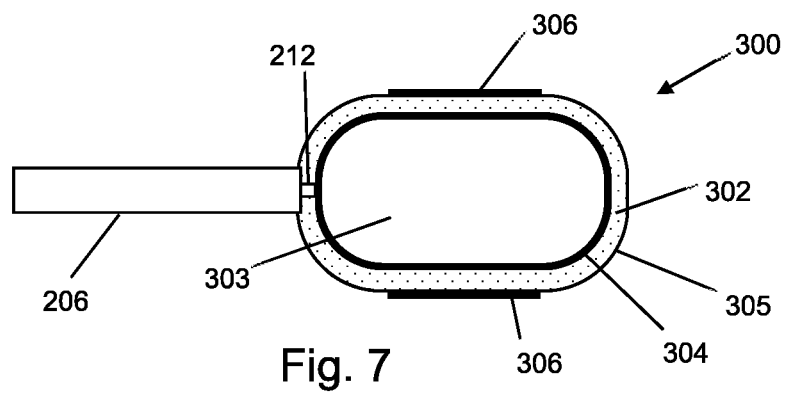
FIG. 7 shows another expandable balloon applicator structure suitable for use in an electrosurgical instrument that is an embodiment of the invention.

FIG. 7 shows a schematic, partial cross-sectional view of an applicator 300 that can be used in an electrosurgical instrument according to another embodiment of the invention. As above, features in common with previous examples are given the same reference numbers and are not described again. The sleeve and inflation channel are omitted for clarity. In this example, the inner conductor 212 of the coaxial cable 206 is connected to a conductive covering on an expandable inner surface 304 that defines an inflatable volume 303. The inner surface 303 is separated from an outer surface 305 by a layer of dielectric material 302. The outer layer 305 may have one or more conductive elements 306 formed thereon. These conductive elements 306 may be dimensioned to act as radiating antennas, e.g. radiating patches or the like.

The layer of dielectric material 302 may itself be the inflatable skin 201 discussed above, i.e. the inner surface 304 and the outer surface 305 are simply opposite surfaces of the same piece of expandable material. However, in another embodiment, the inner surface 304 and outer surface 305 may be provided on separate layers of material, having the dielectric 302 sandwiched between. In this example, the structure may resemble a balloon within a balloon (i.e. an inflatable balloon formed by surface 304 nested inside an outer balloon formed by surface 305. The dielectric material 302 may be fluid. It may have a fixed volume, or it may be separately inflatable, e.g. to control a distance between the inner conductive surface 304 and outer conductive elements 306.

The examples discussed above all relate to applicators in which an expandable balloon is used as part of an energy delivery structure. However, the invention need not be limited to the use of an inflatable balloon. Alternative structures for delivering microwave energy are now discussed with reference to FIGS. 8 to 13.

Figure 8A:
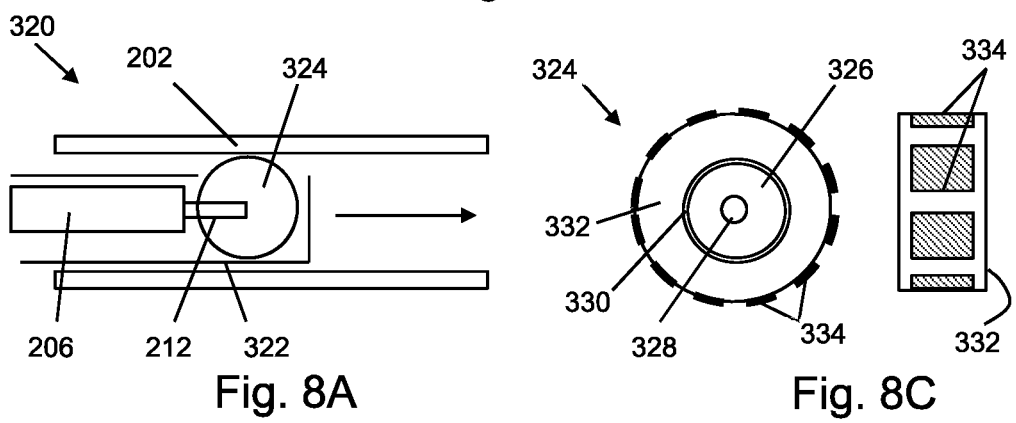
FIGS. 8A and 8B show a schematic side view of a distal end assembly for an electrosurgical instrument that is another embodiment of the invention.
Figure 8C:
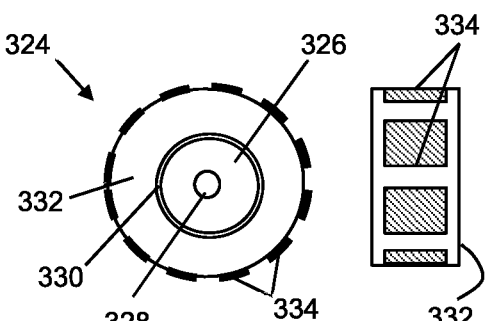
FIG. 8C shows schematic side and front views of a rotatable member suitable for use in the distal end assembly shown in FIGS. 8A and 8B.
Figure 8B:
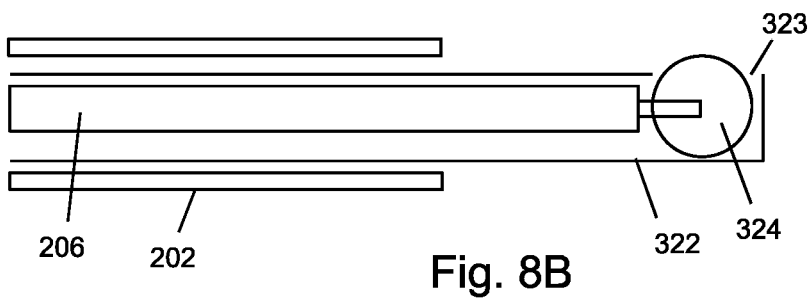

FIGS. 8A and 8B show the schematic partial cross-sectional views through an applicator 320 that is suitable for use in an electrosurgical instrument that is an embodiment in the invention. Instead of using an inflatable balloon, the applicator 320 has a rotatable radiating wheel 324 that can be extended and retracted out of a sleeve 202 mounted within an instrument channel of a surgical scoping device. FIG. 8A shows the applicator 320 in a retracted configuration, where the radiating wheel is inside the sleeve 202. FIG. 8B shows the applicator 320 in an extended configuration, where the radiating wheel 324 is outside the sleeve 202, where it can contact adjacent biological tissue. The radiating wheel 324 is rotatably mounted in a housing 322 that is slidable within the sleeve 202. The housing 322 has an aperture 323 at a distal end thereof from which the radiating wheel 324 projects. In this example the aperture 323 is at one side of the distal end of the housing 322. However it can be located in other positions.

The radiating wheel 324 may have any suitable shape. It may be a sphere, cylinder or other rotationally symmetric object. The axis of rotation of the radiating wheel 324 may be part of the energy conveying structure. For example, the axis of rotation may be connected to the inner conductor 212 of a coaxial cable 206 that is conveyed through the housing 322. Alternatively, a separate axle may be mounted in the housing 322, and a different means of connecting to the coaxial cable can be used.

FIG. 8C illustrates schematically a suitable structure for the radiating wheel in one example. FIG. 8C shows schematic side and front views of a suitable radiating wheel structure 324. In this example, the wheel structure comprises a cylinder or disc having an inner hub 326 with a bore 328 for receiving an axle so that the hub can rotate relative to the housing 322. An outer surface of the hub 326 has a layer of conductive material 330 formed thereon, which is exposed as an electrically conductive ring 330 on one or both sides of the wheel. The inner conductor 212 of the coaxial cable 206 is shaped to contact the conductive ring 330. As the wheel 324 rotates, the point of contact between the ring 330 and the inner conductor remains, even though the wheel is rotating relative to the coaxial cable. An annular piece of dielectric material 332 is provided on top of the conductive ring 330. On the outer surface of the dielectric annular piece 332 are a plurality of electrically conductive patches 334, which may be grounded. The thickness of the dielectric layer 332 and the dimensions of the patches 334 are selected so that the patches 334 radiate microwave energy delivered through the coaxial cable.

The device shown in FIGS. 8A, 8B and 8C may be suitable for ablating a longitudinal strip of GI tract biological tissue by causing longitudinal movement of the housing 332 relative to the sleeve 202 while microwave energy is delivered through the coaxial cable. In other examples, the rotation axis of the radiating wheel can be different, e.g. to permit treatment of a circumferential strip of tissue.

FIGS. 9A and 9B show a schematic side view of an applicator 350 that can be used in an electrosurgical instrument that is embodiment of the invention. In this example, the applicator includes a paddle structure that can be moved longitudinally through the instrument channel (or sleeve 202) of a surgical scoping device. The paddle may be radially movable between a flat configuration (shown in FIG. 9A) where it has a profile that can fit inside the instrument channel or sleeve 202 and a radially extended configuration (shown in FIG. 9B) where it can be brought into contact with biological tissues surrounding the distal end of the instrument cord.

As shown in FIG. 9B, the applicator 350 comprises a paddle 352, which can be a strip of rigid dielectric material onto which is mounted or fabricated a radiating structure 354. The radiating structure 354 may be a bipolar structure having a pair of parallel conductive strips separated by a dielectric material. The conductive strips may be electrically connected by suitable conductive traces (not shown) to an inner and outer conductor of a coaxial cable 206 that is mounted within the sleeve 202. To move the paddle 352 between the flat and radially extended configurations, a pantograph-type hinge mechanism 356 is provided between the coaxial cable and the paddle 352. The pantograph structure may be formed from a pair of cooperating hinge elements (which may be living hinges formed form a suitable rigid material, e.g. stainless steel). The structure can be operated by a pull rod 358 that extends through the sleeve.

FIGS. 10A and 10B illustrate an applicator structure 360 that operates on the same principal as that shown in FIGS. 9A and 9B. Features in common between these two examples are given the same reference numbers and are not described again. In FIGS. 10A and 10B, there are four paddles arranged to radially extend in directions that are angularly spaced by 90° from one another, as shown in the front view of the device depicted in FIG. 10B. The shape of the applicator 360 when in a flat configuration is shown by dotted lines 362 in FIGS. 10A and 10B.

The paddle examples discussed above may be adapted to include an inflatable balloon, e.g. mounted on the paddle 352 and having the radiating structure 354 secured thereto. Inflation of the balloon may be controlled independently of the radial movement mechanism, to enable additional pressure to be applied to the treatment region.

FIGS. 11, 12 and 13 relate to applicator structures in which microwave energy is delivered from one or more radiating elements fabricated on a flexible substrate. The radiating elements may be patch antennas, for example. In one example, the flexible substrate represents a dielectric layer, which has a conductive layer (e.g. formed from a layer of metallisation) connected to an inner conductor of a coaxial cable on one side, and one or more conductive patches (which are grounded or electrically floating) formed on an opposite side. The conductive patches may be discrete portions of metallisation formed on the flexible substrate (with connecting traces on or below the substrate surface). The dimensions of the patches of conductive material are selected so they radiate microwave energy delivered through the coaxial cable.

The flexible substrate may be movable between a storage configuration in which it is suitable for insertion through the instrument channel of a surgical scoping device and a deployed position in which it is suitable for delivering microwave energy into biological tissue forming the wall of the GI tract.

FIG. 11 shows one example of an applicator structure 380 that uses a flexible substrate. The applicator structure comprises a catheter 382 that is slidably mounted in a longitudinal sense within the instrument channel of surgical scoping device (e.g. gastroscope). The catheter 382 may be slidably mounted in a sleeve 202 that extends through the instrument channel, or may be mounted in the instrument channel alone. A coaxial cable 206 for conveying microwave energy extends along the length of the catheter. A distal end of the coaxial cable terminates with a sheet of flexible dielectric material 384, such as Rflex®, manufactured by Rogers Corporation. A longitudinal slot 385 is formed in a side surface of the catheter 382. The slot is dimensioned to permit the flexible dielectric sheet 384 to pass therethrough so that it is exposed on the outside of the catheter 382. The flexible dielectric sheet 384 may be rotatable about the axis of the catheter between a coiled configuration in which it is contained within the catheter 382, and a deployed (or unfurled) configuration where it has passed through the slot 385 and is located round part or all of the circumference of the catheter 382.

The flexible dielectric sheet 384 may be preformed in a curved manner so that it preferentially coils around the body of the catheter 382 when in the unfurled configuration.

One surface of the flexible dielectric sheet 384 has a plurality of electrically conductive patches 386 formed in a regularly spaced array thereon. The patches may be metallised regions of the dielectric surface. On an opposite side of the flexible dielectric sheet 384 (not shown in FIG. 11) an unbroken layer of conductive material (e.g. metallisation) is formed behind the array of conductive elements 306. The unbroken conductive layer is electrically connected to the inner conductor of the coaxial cable 206. The electrically conductive patches 386 are dimensioned to act as radiating elements for microwave energy supplied through the coaxial cable. The radiating elements are located on the outwardly facing surface of the flexible dielectric sheet 384 when it is in the unfilled configuration.

FIG. 12A shows a schematic view of an applicator 400 that has a different deployment mechanism for a flexible substrate 384. In this example, the flexible substrate 384 is attached to the distal end of a coaxial cable. A sleeve 402 is mounted around the coaxial cable 206. The sleeve 402 and coaxial cable 206 are slidable relative to one another so that the flexible substrate 384 passes through a distal mouth 406 of the sleeve 402. The flexible sheet 384 has a pair of proximally facing curved surfaces 404 which engage with the mouth 406 in a manner that causes the flexible sheet to adopt a rolled configuration, as shown in FIG. 12C. The diameter of the rolled portion may depend on how much of the flexible sheet is located within the sleeve 402.

FIG. 12B shows an alternative shape for the flexible sheet 304. In this example, the flexible sheet has one flat longitudinally extending edge and one curved proximally facing edge 408 that is arranged to engage the mouth 406 of the sleeve 402 to cause the flexible sheet to adopt the rolled configuration shown in FIG. 12C.

For the flexible applicators discussed above, it may be desirable also to include a means for controlling the shape or position of the flexible sheet, e.g. to force it to adopt a certain position, such as facing against the tissue to be treated.

These applicators may thus include a sheet shape control mechanism. This may take any suitable form. For example, it may comprise a radially coiled spring that is adapted to urge the flexible sheet outwards. A control rod may be provided to enable the spring to be retracted, e.g. during insertion through the sleeve. In another example, the sheet shape control mechanism may comprises one or more bimetallic elements, e.g. applied to the back face of the flexible sheet. In a third example, the sheet shape control mechanism may comprise a coiled balloon that is adapted to unfurl upon inflation. The flexible sheet may be secured to the balloon so that it adopts the required position upon inflation of the balloon.

Figure 13A:
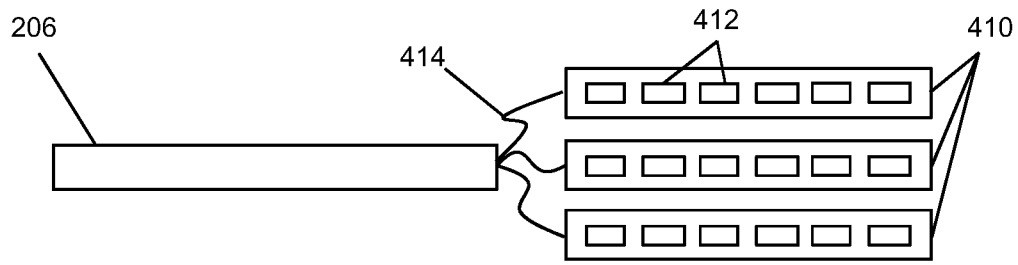
FIGS. 13A, 13B, 13C and 13D are schematic side views of distal end applicators comprising flexible substrate strips and radiating elements formed thereon, which can be used in electrosurgical instruments that are embodiments of the invention.

In the examples above, the radiating elements were fabricated in an array over the surface of a sheet of flexible dielectric material. In other examples, the flexible substrate material may be provided as one or more strips which have a line of radiating elements formed there along. FIG. 13A illustrates a schematic representation of this idea. In FIG. 13A there are three strips 410 formed of flexible dielectric material. Each strip has a line of electrically conductive material formed on a back surface (not shown) thereof which is connected to the inner conductor of a coaxial cable 206 by suitable wiring or traces 414. On the front surface of each strip 410 a line of electrically conductive patches 412 is formed. The electrically conductive patches 412 are configured to act as radiating elements in a manner similar to those discussed above.

In applicator structures that are suitable for use in electrosurgical instruments according to the invention, one or more of such flexible strips may be used, as discussed below.

Figure 13B:
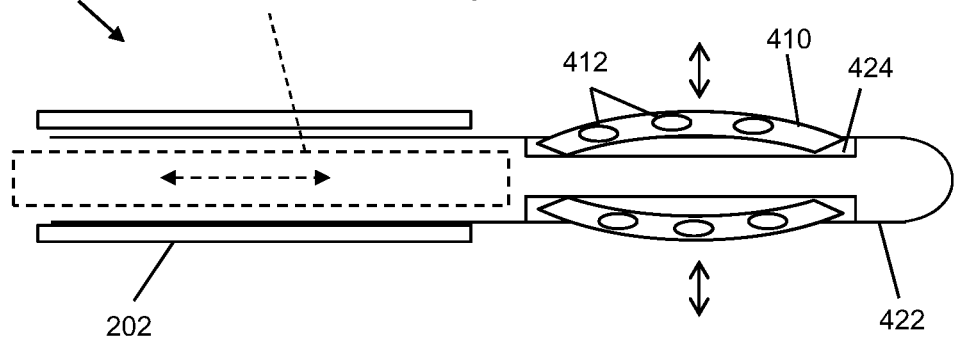

FIG. 13B shows an applicator structure 420 that is suitable for use in an electrosurgical instrument that is an embodiment of the invention. The applicator structure 420 makes use of flexible substrate strips 410 as discussed above with respect to FIG. 13A. In this example, the applicator structure 420 comprises an elongate probe housing 422 that is slidably mounted within the instrument channel of a surgical scoping device. The probe housing 422 may have a rounded distal tip to prevent damage from occurring when it is inserted into position. The probe housing 422 may be mounted in and slidable relative to a sleeve 202 that is present within the instrument channel, or it may be inserted directly into the instrument channel without any surrounding support.

In the example shown in FIG. 13B, a plurality of longitudinal slots 424 are formed at a distal portion of the probe housing 422. The longitudinal slots 424 are sized to permit a flexible strip 410 having a plurality of radiating elements 412 formed thereon to pass through and protrude radially therefrom.

The flexible strips 410 are moveable between a flat configuration in which they are located within the body of the probe housing 422 and a deployed configuration (shown in FIG. 13B) in which they protrude outside the longitudinal slots 424 e.g. to contact biological tissue and deliver microwave energy thereto. In order to move between these two positions, the flexible strips 410 are attached at their proximal ends to a slidable control rod that is mountable within the probe housing. In one example, the slidable control rod is the coaxial cable 206 that supplied microwave energy to the radiating structure.

Figure 13C:
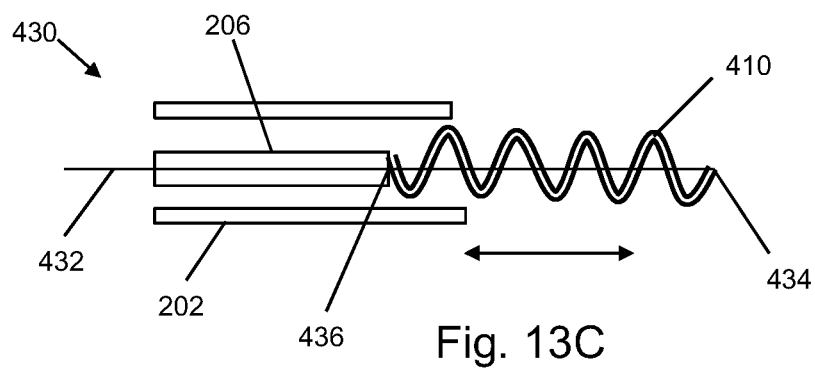

FIG. 13C is a schematic side view of an applicator structure 430 that is suitable for use in an electrosurgical instrument that is an embodiment of the invention. The applicator structure 430 uses a flexible strip 410 as discussed above wound in a helical coil configuration around a longitudinal axis of the device. The radiating elements (not shown in FIG. 13c) are arranged to face radially outwardly from the helical coil. In this example, the material used for the flexible substrate may be selected to ensure that the helical coil possesses sufficient rigidity for it to hold its shape in use. The coil structure may be slidably mounted in a sleeve 202 that extends through the instrument channel of a surgical scoping device. In one example, the diameter of the coil structure may be variable, e.g. by controlling the distance between a distal end 434 of the coil structure and a proximal end 436 of the coil structure. The proximal end 436 may be where the coil structure meets (e.g. is attached to) a distal end of a coaxial cable 206. The distal end 434 of the coil structure may be attached to a control rod 432 that is slidable relative to the proximal end 436. Moving the ends of the coil structure closer together may cause the turns in the coil to increase in diameter. Thus, when the coil structure is in a deployed position, i.e. outside the instrument channel and/or sleeve 202, the control rod 432 can be used to bring the radiating structures closer to the biological tissue to be treated.

Figure 13D:
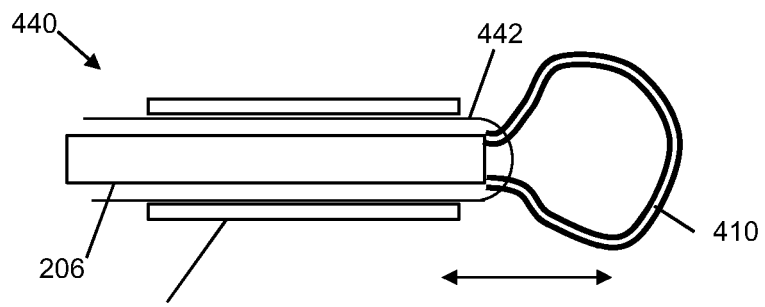

FIG. 13D shows an applicator structure 440 that can be used in an electrosurgical instrument that is an embodiment of the invention. The applicator structure 440 uses a flexible strip 410 as discussed above. In this example, the flexible strip 410 forms a loop that can be extended and retracted from a probe housing 442. The probe housing 442 may be slidably mounted in the instrument channel of a surgical scoping device in a similar manner to the examples discussed above. The probe housing may have a pair of apertures in a distal surface thereof through which two ends of the loop pass. The flexible strip 410 can be drawn into the housing through these apertures through operation of a slidable control rod mounted inside the probe housing 412. In one example, the control rod can be the coaxial cable 206.

Figure 14:
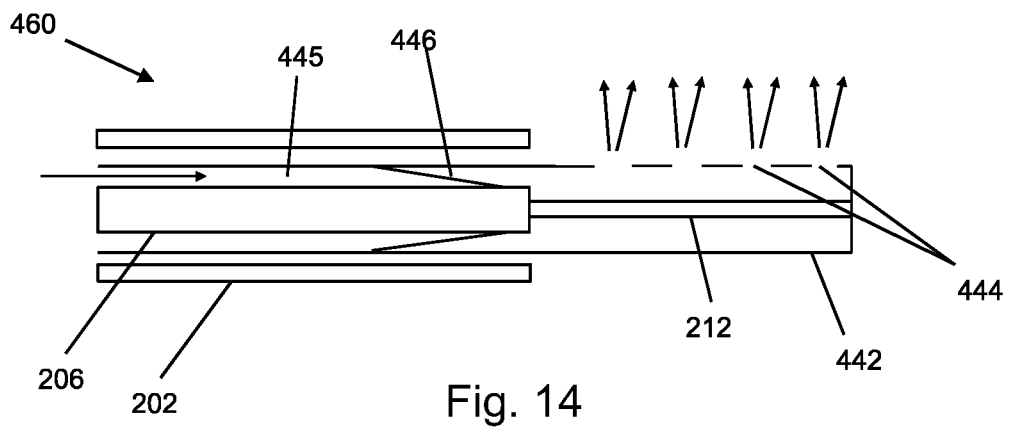
FIG. 14 is a schematic side view of a distal end assembly for an electrosurgical instrument in which plasma is used to deliver energy into biological tissue.

FIG. 14 shows a schematic side view of an applicator 460 that can be used in an electrosurgical instrument that is an embodiment of the invention. In this example, energy is delivered into biological tissue through a plasma that can be struck at the distal end of the instrument. The applicator comprises a probe housing 442 that is slidably mounted within an instrument channel of a surgical scoping device, e.g. alone or in conjunction with a guiding sleeve 202. The probe housing defines an internal lumen which carries a coaxial cable 206 and forms a gas flow path 445. A proximal end of the probe housing 442 is connected to a supply of gas, e.g. argon or the like. At a distal end of the probe housing 442, one or more slots 444 or apertures may be formed in the side walls thereof to permit the gas to escape. The coaxial cable 206 is arranged to convey microwave energy to the distal part of the probe housing 442. An outer conductor of the coaxial cable is electrically connected to the probe housing 446 by one or more connectors 446. The inner conductor 212 of the coaxial cable protrudes beyond a distal end of the outer conductor (e.g. outer conductor 209) and is electrically connected to a distal tip of the probe housing 442. This arrangement causes a short circuit condition that sets up an electric field within the probe housing 442. The slots 444 are located at expected maxima in the electric field so that a plasma can be struck from gas supplied along the gas flow path 445.

Figure 15:
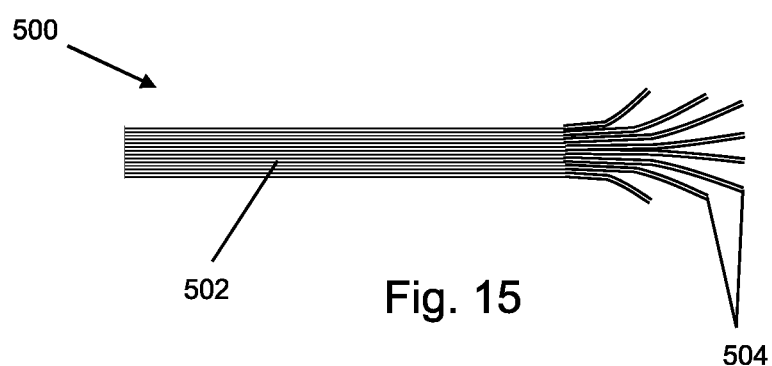
FIG. 15 is a schematic side view of a distal end assembly formed from a plurality of graphene cables.
Figure 16:
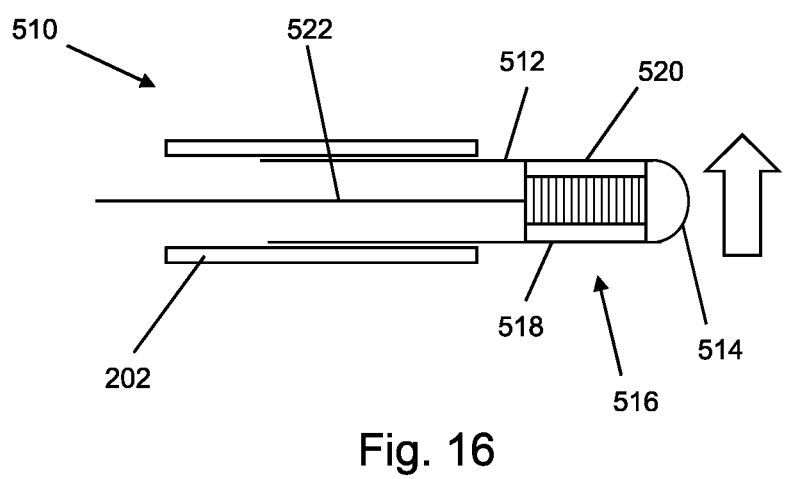
FIG. 16 is a schematic view of a distal end assembly for an electrosurgical instrument that incorporates a thermoelectric cooling device.

The applicator structures discussed above are concerned with ways of delivering microwave energy into tissue. FIGS. 15 and 16 present applicator structures that can use different forms of energy.

FIG. 15 is a schematic side view of an applicator 500 that is suitable for use with the invention. The applicator 500 comprises a bundle 502 of graphene cables. The cable bundle 502 may have a length suitable to pass through the instrument channel of a surgical scoping device. For example, it may be equal to or greater than two metres in length. Graphene cables are known to transmit thermal energy very efficiently. Thus, a proximal end of the cable bundle 502 is in thermal communication with a heat source (not shown). Thermal energy from the heat source can be conveyed by the bundle of cables through the instrument channel with very little loss, thereby limiting or minimising the risk of unwanted endoluminal heating.

At a distal end of the cable bundle 502 the individual graphene cables 504 are separated out into a brush structure that can be manipulated to direct the heat transferred through the cable 502 into biological tissue.

FIG. 16 shows a schematic side view of an applicator structure 510 that can be used in the invention. The applicator 510 makes use of the thermoelectric cooling effect to transfer heat between opposite sides of a distal tip to induce cooling and/or heating effects in biological tissue. The applicator 510 comprises a probe 512 that is slidably mounted within an instrument channel of a surgical scoping device. The probe 512 may be mounted directly in the instrument channel, or may be held within a suitable sleeve 202. The probe 512 has a rounded distal tip 514 to prevent tissue damage when the probe is moved into position. A thermoelectric device 516 is mounted in a distal portion of the probe 512. The thermoelectric device 516 has a pair of thermally conducting plates 518, 520 arranged on opposite sides of the probe 512. The thermally conducting plates 518, 520 are separated by a semiconductor structure that is adapted to use the Peltier effect to create a heat flux between the plates 518, 520 on application of a current thereto. The current is provided from a suitable DC source at the proximal end of the device via a cable 522.

Whilst it may be possible to manufacture the applicator structures disclosed above in a size suitable for insertion through an instrument channel in an endoscope, it may in some cases be desirable for the applicator structure to be larger. Indeed, given the lay-up construction, complexity and consequent bulk of some structures, it may not be possible to feed them through the instrument channel of a typical GI flexible video endoscope from its proximal end. The disclosure herein contemplates a number of alternative means of introduction and control for such applicator structures. Examples of such structures are discussed below with reference to FIGS. 17 to 20. It is to be understood that these ideas may find applicability in any GI trans-oral or rectal procedure where a flexible endoscope and visualisation is required, and where the distal applicator construction is such that it prevents its introduction through the instrument (or working) channel of a flexible GI endoscope.

Figure 17:
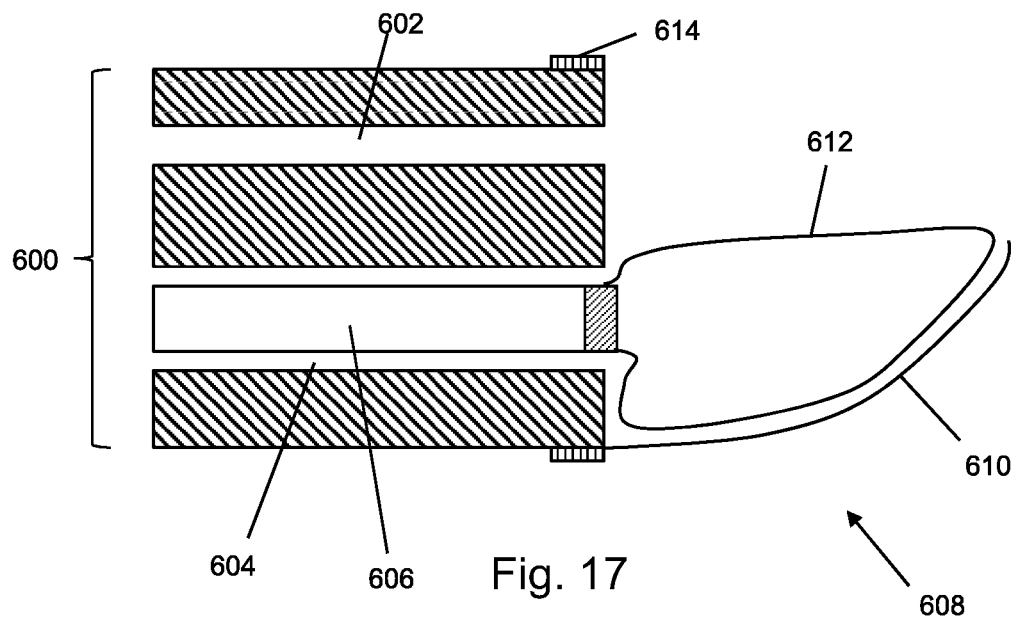
FIG. 17 is a schematic side view of a distal mounted assembly that can be used with the present invention.
Figure 18:
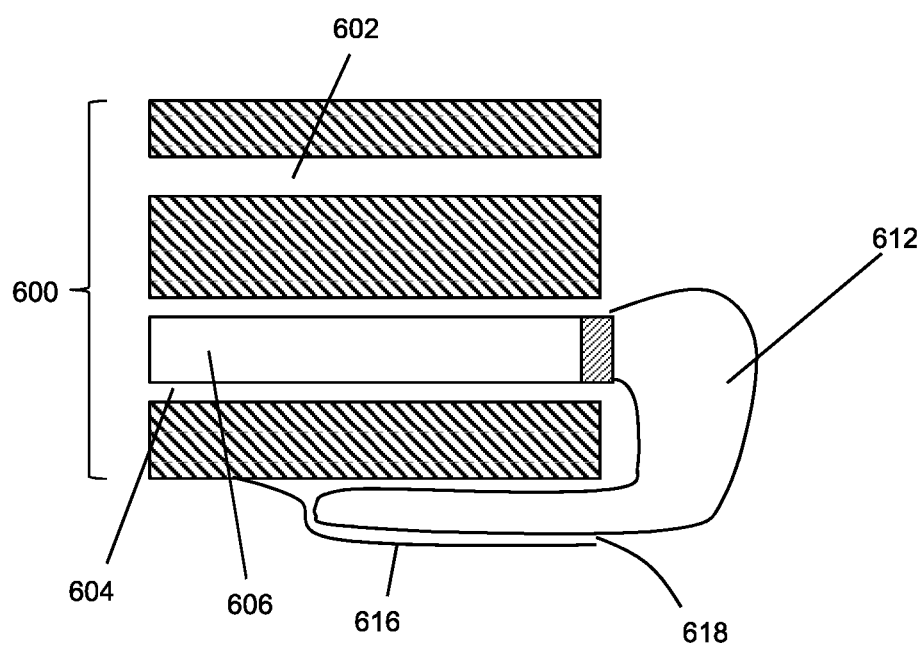
FIG. 18 is a schematic side view of another distal mounted assembly that can be used with the present invention.

FIGS. 17 and 18 relate to carrier structures for an applicator (e.g. any of the applicators discussed above) that can be mounted at the distal end of an instrument cord before insertion into a patient.

FIG. 17 is a schematic cross-sectional view through a distal end of an instrument cord 600 of a surgical scoping device (e.g. endoscope or gastroscope). The instrument cord comprises one or more visualisation lumens 602 for conveying optical signals to and from a treatment region, and an instrument channel 604 (also referred to herein as a working channel) for conveying a probe 606 to the treatment region.

In FIG. 17, a carrier 608 for an applicator 612 takes the form of a conformal clip-on attachment that can be mounted on or around the distal end of the instrument cord 600. The carrier 608 has a cup portion 610 that projects forward to form a recess in which the applicator 612 (which may be a collapsed balloon and any other of the distal applicator assemblies discussed herein) is nested. The cup portion presents a smooth outer curved conformal profile to the patient for introduction. The folded/collapsed applicator 612 can be positioned against and/or clipped to the inner face of the cup portion 610 in such a way as to avoid obscuring the visualisation lumen(s) 602 to ensure good visibility during introduction.

The cup portion 610 is secured to the distal end of the instrument cord 600 by a clip 614. The probe 606 is inserted through the working channel 604 before the instrument cord 600 is inserted into a patient. This may be done by feeding the probe 606 (which may comprise a multi-luminal shaft as discussed above) back up the working channel 604 from the distal end. After this, the proximal connections of the probe may be made, and the carrier 608 attached to the distal end of the instrument cord 600 before the instrument cord 600 is introduced into a patient. In an alternative set up, the applicator 612 may be attached to a distal end of probe 606, e.g. at the same time as attaching the carrier 608.

Once at the treatment site the applicator 612 can be deployed and used in a location just forward of the cup portion 610 or drawn back over the cup portion wherein the cup portion can act as a shield for treatment.

Withdrawal of the device from the patient is performed by switching the applicator 612 into a retracted or reduced volume configuration (e.g. by deflating a balloon) before drawing both the instrument cord 600 and the in situ applicator 612 from the patient simultaneously.

FIG. 18 is a schematic cross-sectional view through a distal end of an instrument cord 600 of a surgical scoping device (e.g. endoscope or gastroscope). Features in common with FIG. 17 are given the same reference number and are not described again.

In FIG. 18, a carrier 616 is provided on or around the distal end of the instrument cord 600 such that its most distal end is effectively flush with the end of the instrument cord. The carrier 616 is a wall mounted on the outside of the instrument cord 600 to define a pocket 618 for retaining the applicator 612. The pocket 618 may extend around all or part of the circumference of the instrument cord 600. The outer profile of the pocket may be smooth and conformal to aid introduction. The applicator 612 sits within the pocket 616 and it connected to the probe 606 that is fed back up through the working channel 604 for proximal connection. Operation and withdrawal of the applicator are the same as discussed above with reference to FIG. 17.

Figure 19:
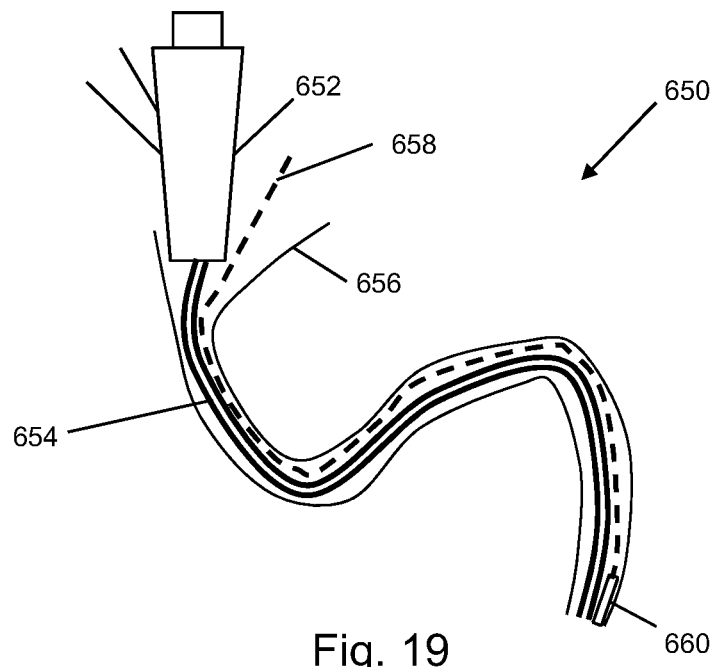
FIG. 19 is a schematic view of a carrier sleeve that can be used with the present invention.

FIG. 19 is a schematic partial cross-sectional view of a carrier system 650 that is suitable for use with the invention. The system comprises a surgical scoping device that has a body 652 with a flexible instrument cord 654 extending therefrom. The carrier system 650 in this example provides a flexible sleeve 656 that fits over the full length of the instrument cord, either concentrically or eccentrically.

The sleeve 656 provides a custom external conduit for conveying one or more required feeds, e.g. inflation medium, coaxial cable, control wires, etc. to a distal applicator 660. The applicator 660 may be mounted to a distal end of the sleeve 656 using one of the carrier structures discussed above with reference to FIG. 17 or 18. The sleeve 656 may be an integral part of the applicator 660 or a separate component.

In use, the sleeve 656 with collapsed applicator 660, e.g. mounted within a carrier, is first fed over the flexible instrument cord 654 before insertion into the patient.

With this arrangement, the feeds for the applicator are not constrained to lie within the working channel of the instrument cord. This may enable the device to be used with a much smaller diameter flexible video scope. For example, the sleeve may be used with a scoping device that does not have a working channel. Alternatively, if used with a scoping device that has a working channel, the working channel may be used for introduction of a separate (additional) instrument.

Figure 20:
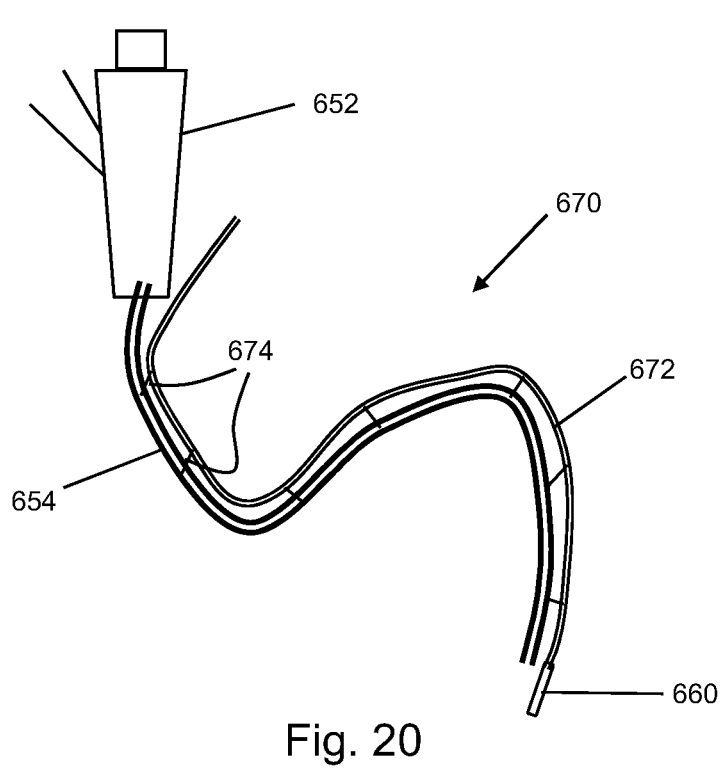
FIG. 20 is a schematic view of another carrier sleeve that can be used with the present invention.

FIG. 20 is a schematic partial cross-sectional view of a carrier system 670 that is suitable for use with the invention Features in common with FIG. 19 are given the same reference number and are not described again.

In this example, a carrier sleeve 672 for conveying feeds for the applicator 660 is secured (e.g. clipped) to the instrument cord 654 of the surgical scoping device. The carrier sleeve 672 may comprise a multi-lumen shaft tube, ideally of low profile layout. It may secured to the instrument cords by a plurality of clips 674 at intervals along its length. A carrier (not shown) similar to that discussed above with reference to FIGS. 17 and 18 may be mounted at a distal end of the carrier sleeve 672 and clipped to the distal end of the instrument cord 654.

As discussed above, the carrier and carrier sleeve 672 may provide a compact location for introduction of the combined instrument cord 654 and applicator 660 into the patient, whilst ensuring good operator visibility during introduction. By providing low profile and smooth conformal outer form, the carrier assembly and clips can ensure minimal discomfort to patient during introduction.

Similarly to the system shown in FIG. 19, the carrier system 670 does not make use of the scope working channel, which means that either a smaller diameter scope (without working channel) can be used, or that the working channel can be used for a different purpose, e.g. separate instrument or other type of feed, e.g. fluid.

In another examples, the apparatus of the invention may comprise a flexible introducer for insertion into a patient to carry the applicator to a treatment site. The flexible introducer may obviate the requirement for a separate flexible endoscope. The flexible introducer may comprise a sleeve that can enclose the coaxial cable. Alternatively, the flexible introducer may comprise a flexible rod or spine to which the feed lines associated with the applicator can be attached. The flexible introducer may be steerable, e.g. may have one or more control wires extending along its length. The introducer may be formed separately from or integrally with the applicator.

The introducer may include an internal optics channel for conveying optical radiation to a from the treatment site. For example, the introducer or applicator may comprise a camera mounted at the distal end of the apparatus. The optics channel may include optical fibres for conveying an illumination signal and an image signal from the camera.

Providing a bespoke introducer for the applicator may enable a larger diameter working channel to be provided for conveying the applicator and associated feed lines. The introducer may be disposable or low volume reposable.

The apparatus need not be used with a scoping device that provides direct visualisation of the treatment region. For example, the apparatus may be used with an ultrasound scanner or similar type external visualisation means. The flexible introducer or cannula used in such an example, may comprise marker graduations along its length in proximal and distal regions thereof. The distal markings may be radiopaque to improve visibility on scanned images. The markings can thus be used as positional reference for treatment.

REFERENCES

[1] Cherrington, et al. 13th World Congress on Insulin Resistance, Diabetes & Cardiovascular Disease. Los Angeles, Calif., USA, December 2015.

The invention claimed is:

1. An electrosurgical instrument configured to ablate duodenal mucosal tissue, the instrument comprising:
a flexible coaxial cable for conveying microwave energy from a generator located externally to a patient to a treatment site located inside a duodenum of the patient;
an applicator located at a distal end of the flexible coaxial cable, the applicator having an energy delivery structure connected to receive microwave energy from the coaxial cable and to deliver the received microwave energy into duodenal mucosal tissue at the treatment site,
wherein the applicator includes a single radially extendable balloon arranged to move the energy delivery structure into contact with duodenal mucosal tissue at the treatment site, wherein the balloon is formed by a single layer of balloon skin which defines a volume enclosed by the balloon,
wherein the energy delivery structure comprises:
an internal conductive element disposed within the volume enclosed by the balloon, the internal conductive element being electrically connected to an inner conductor of the flexible coaxial cable to launch the microwave energy into duodenal mucosal tissue at the treatment site; and
an outer conductive structure formed on an outer surface of the balloon, the outer conductive structure being electrically connected to an outer conductor of the flexible coaxial cable,
wherein the internal conductive element is an extension of the inner conductor of the coaxial cable, and
wherein the energy delivery structure comprises a bipolar emitting structure formed by the outer conductive structure and the internal conductive element.

2. The electrosurgical instrument according to claim 1, wherein the flexible coaxial cable includes an inflation channel arranged to deliver an inflation medium into a volume enclosed by the balloon.

3. The electrosurgical instrument according to claim 2, wherein the internal conductive element comprises a portion of an inner conductor of the flexible coaxial cable that protrudes into the volume enclosed by the balloon to form a monopole antenna for launching the microwave energy into duodenal mucosal tissue at the treatment site.

4. The electrosurgical instrument according to claim 1, wherein the outer conductive structure has a plurality of radiating slots formed therein.

5. The electrosurgical instrument according to claim 1, wherein the internal conductive element is electrically connected to the outer conductive structure at a distal end of the balloon.

6. An electrosurgical apparatus for ablating duodenal mucosal tissue, the apparatus comprising:
a surgical scoping device having an instrument cord for insertion in a patient to a treatment site located inside a duodenum of the patient;
the generator for suppling microwave energy;
the electrosurgical instrument according to claim 1, and wherein the flexible coaxial cable is connected at its proximal end to the generator, wherein the flexible coaxial cable and applicator are insertable together with the instrument cord to the treatment site.

7. The electrosurgical apparatus according to claim 6, wherein the instrument cord has a longitudinal instrument channel running therethrough, and wherein the flexible coaxial cable and applicator are dimensioned to be slidably mounted in the instrument channel.

8. The electrosurgical instrument according to claim 1, wherein an inflation medium for the balloon is low density PTFE or a foam.

\* \* \* \* \*